United States Patent [19]

Anderson et al.

[11] Patent Number: 5,502,660
[45] Date of Patent: Mar. 26, 1996

[54] DYNAMIC GAS DENSITY COMPENSATION IN PULMONARY GAS ANALYZER SYSTEMS

[75] Inventors: David M. Anderson, St. Paul; Shawn McCutcheon, White Bear Lake, both of Minn.

[73] Assignee: Medical Graphics Corporation, St. Paul, Minn.

[21] Appl. No.: 217,153

[22] Filed: Mar. 24, 1994

[51] Int. Cl.$^6$ .................................................. G01L 27/00
[52] U.S. Cl. .................... 364/571.03; 73/4 R; 73/861.01; 364/571.01; 364/571.02; 364/571.04
[58] Field of Search ................... 73/4 R, 861.01, 73/861.42; 128/671, 725; 364/571.01, 571.02, 571.03, 571.04, 571.08

[56] References Cited

U.S. PATENT DOCUMENTS

| | | | |
|---|---|---|---|
| 3,026,868 | 3/1962 | Weinberg | 128/725 |
| 4,386,604 | 6/1983 | Hershey | 128/718 |
| 4,463,764 | 8/1984 | Anderson et al. | 128/725 X |
| 4,754,651 | 7/1988 | Shortridge et al. | 73/861.42 |
| 4,911,021 | 3/1990 | Shortridge et al. | 73/861.66 |
| 5,038,773 | 8/1991 | Norlien et al. | 128/725 X |

Primary Examiner—Edward R. Cosimano
Attorney, Agent, or Firm—Haugen and Nikolai

[57] ABSTRACT

A method is described for dynamically calibrating a flowmeter used in cardiopulmonary performance analyzing equipment which takes into account the ambient conditions at the test site in terms of relative humidity, barometric pressure and temperature. At the time of factory calibration, a density factor is computed and stored in a nonvolatile memory along with a calibration factor obtained by passing a known volume of gas at a known relative humidity, temperature and pressure through a pneumotach mouthpiece in a predetermined time span. When the system is being used in the field to evaluate a patient, a new density factor is computed that takes into account the relative humidity, barometric pressure and temperature at the test site and this new density factor along with the density factor previously computed and stored at factory calibration are used to compute a new flow calibration factor for use in obtaining an accurate flow parameter from the system flowmeter.

5 Claims, 1 Drawing Sheet

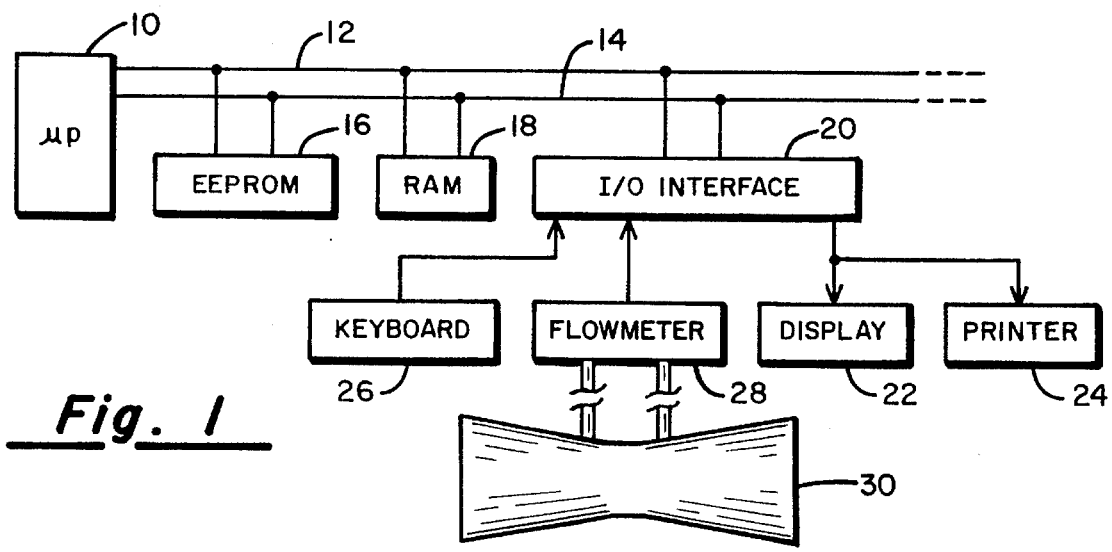
Fig. 1
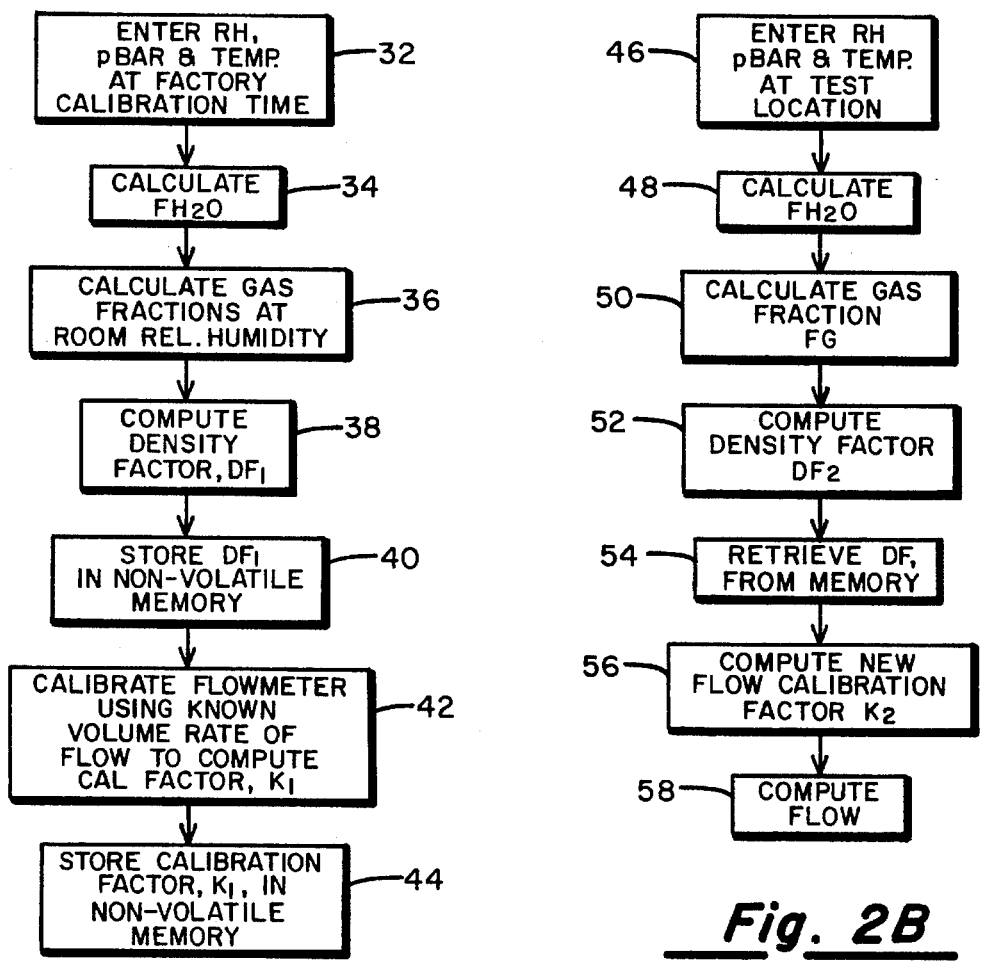
Fig. 2A
Fig. 2B

DYNAMIC GAS DENSITY COMPENSATION IN PULMONARY GAS ANALYZER SYSTEMS

BACKGROUND OF THE INVENTION

I. Field of the Invention

This invention relates generally to cardiopulmonary performance analyzing systems, and more particularly to a method for automatically and dynamically calculating a proportionality constant for a flow meter used in the system so as to adjust for changes in ambient conditions, including barometric pressure, temperature and relative humidity, all of which effect the density of the respiratory gases being analyzed.

II. Discussion of the Prior Art

In the Anderson et al. U.S. Pat. No. 4,463,764, there is described a cardiopulmonary exercise system including a plurality of gas sensors connected to a sample line for measuring the percentage concentration of discrete gases in an air mixture being breathed. It also incorporates a flow meter having a pneumotach patient mouthpiece coupled by tubing to a differential pressure sensor for measuring respiratory flow, both inspiratory and expiratory. The gas sensors and the pressure sensor each provide an analog output to a microprocessor-based waveform analyzer. The microprocessor is programmed to process the sensor-derived information for providing a variety of cardiopulmonary performance parameters used by physicians for evaluating the physiologic condition of the patient.

As those skilled in the art appreciate, the flow readings obtained from the differential pressure sensor are subject to variations due to changes in ambient conditions, including barometric pressure, room temperature and relative humidity of the air in the room where testing is underway. Thus, even if the system is accurately calibrated at the factory, using a precision syringe to flow a known volume of air through the flow meter mouthpiece at a known rate and under carefully controllable temperature and relative humidity conditions, the resulting calibration factor, K, used to make the equation:

Calibrated Flow=$K$* Uncalibrated Flow true, is known to vary with changes in ambient conditions. In the past, K has been empirically determined in the field using a syringe. This new technique eliminates the requirement of using a syringe in determining the proportionality factor, K. It is, accordingly, a principal object of this invention to provide a method for accurately adjusting such calibration factor at any time without a syringe and which takes into account differences in ambient conditions prevailing at the site of the test on the patient from those that may have existed at the factory when the system was originally calibrated.

SUMMARY OF THE INVENTION

The method of dynamically calibrating a flowmeter used in a gas measuring system in accordance with the present invention involves measuring the temperature, barometric pressure and relative humidity at a first system calibration time and using those measurements for calculating a first density factor, $DF_1$, of the gas. This step is generally performed at the factory where the gas measuring system is constructed. The calculated density factor, $DF_1$, is stored in a non-volatile memory associated with the microprocessor in the system's waveform analyzer for later retrieval. Also, during factory calibration of the system, the flowmeter is used to measure a known volume rate of flow of a respiratory gas mixture having the calculated density factor, $DF_1$. Next, a proportionality factor, $K_1$, is calculated as the known volume of the respiratory gas mixture divided by the integral of the uncalibrated flow and this proportionality factor is also stored in the non-volatile memory for later use.

With the respiratory gas measuring system in the field being used to actually assess patient cardiopulmonary performance, a second gas density factor, $DF_2$, of the air being breathed at the test site is calculated using a temperature, barometric pressure and relative humidity measured at the test site. Then, the first density factor, $DF_1$, and the proportionality factor, $K_1$, are read out from the non-volatile memory and are used along with the calculated second density factor, $DF_2$, to complete a new proportionality constant for the flowmeter readings, $K_2$, in accordance with the equation:

$$K_2 = K_1 [DF_2/DF_1]^{1.5}$$

The density factor $DF_1$ is computed as the ambient temperature divided by the product of the barometric pressure and the molecular weight of ambient air at factory calibration time. $DF_2$ is calculated identically using ambient air at a second, later calibration time.

DESCRIPTION OF THE DRAWING

The foregoing features, objects and advantages of the invention will become apparent to those skilled in the art from the following detailed of a preferred embodiment in which:

FIG. 1 is a block diagram of the portion of the cardiopulmonary performance analyzing equipment used in carrying out the method of the present invention; and FIGS. 2A and 2B are software flow diagrams of the major steps in carrying out the method of the present invention and useful in writing a program for the microprocessor whereby the method can be implemented.

DESCRIPTION OF THE PREFERRED EMBODIMENT

Referring first to FIG. 1, the waveform analyzer described in the aforereferenced Anderson et al. '764 patent includes a microprocessor 10 having an address bus 12 and a data bus 14 for connecting the microprocessor to a nonvolatile EEPROM memory 16, a RAM memory 18 and an I/O interface module 20. As will be further explained, EEPROM memory 16 is used to store various constants necessary for carrying out certain calculations as well as a software program executable by the microprocessor 10. The RAM memory 18 is a read/write memory used to store operands, partial results and other data. The I/O interface module 20 may include an analog-to-digital converter along with the necessary buffers and drivers for providing inputs to the microprocessor 10 over the data bus 14 and for feeding information to one or more output devices such as a display monitor 22 and a hard copy printer 24. Alternatively, the A/D converter may be a part of the microprocessor 10. Data can be entered into the microprocessor, via a keyboard 26, in a conventional fashion. A flowmeter 28 including a pneumotach mouthpiece coupled to differential pressure sensor also provides an analog voltage proportional to the volume rate of flow of respiratory gas through the patient pneumotach mouthpiece 30 to the I/O interface 20.

Those desiring additional information concerning the construction of a flowmeter system suitable for use in carrying out the method of the present invention are referred to the Norlien et al. U.S. Pat. No. 5,038,773, which is assigned to applicants' assignee. A flowmeter of the type described in the Norlien et al. patent requires that there be a calibration factor for converting the output from the flowmeter electronics into calibrated flow measured in milliliters-per-second. In other words:

$$\text{CALIBRATED FLOW} = K * \text{uncalibrated flow} \qquad \text{Eq. 1}$$

Part of this calibration factor, K, comes from the characteristics of the system electronics which are relatively constant and part thereof comes from the density of the gas being measured which varies. Because of the fact that the calibration factor is not really a proportionality "constant" for accurate performance, it is necessary to take into account changes in temperature, barometric pressure and relative humidity.

With reference first to block 32 in FIG. 2A, at the time that the system is manufactured and calibrated at the factory, either the keyboard 26 of FIG. 1 or sensors built into the equipment are used to enter the existing relative humidity, barometric pressure and temperature into the microprocessor 10. Also loaded into the memory are the known fractions of the various gases found in dry room air, which are as follows:

$FN_2$dry . . . 0.78084

$FO_2$dry . . . 0.20946

$FCO_2$dry . . . 0.00033

ARGONdry . . . 0.00937

Also stored in the memory are the following Gram Molecular Weights for the above gases as found in the standard chemical handbooks:

| GAS | GMW |
| --- | --- |
| $N_2$ | 28.01340 |
| $O_2$ | 31.00080 |
| $CO_2$ | 44.01080 |
| ARGON | 39.94800 |
| $HO_2$ Vapor | 18.01570 |

With the above constants in memory, it possible to calculate the fraction of water vapor from the relative humidity reading (block 34) as:

$$FH_2O = (RH/100) * ppH_2OSat/pBar \qquad \text{Eq. 2}$$

where:

$FH_2O$=Fraction $H_2O$

RH=Relative Humidity (%)

pBar=Barometric Pressure (absolute)

$ppH_2OSat$=Partial Pressure of $H_2O$ in 100% saturated air at given temperature.

Temp=Temperature (degrees Kelvin)

Next, the microprocessor is programmed to calculate the fraction of any gas (FG) at room air relative humidity (block 36), using the equation:

$$FGhum = FG(Dry) * (1 - FH_2O) \qquad \text{Eq. 3}$$

Once the gas fractions of each of the constituents of the air at the room air relative humidity have been computed, it is possible to calculate a density factor, $DF_1$ for the system at the time of factory calibration (block 38). The density factor is computed utilizing the equations:

$$\Sigma GMW = FN_2hum * GMW\_N_2 + FO_2hum * GMW\_O_2 + FCO_2hum * GMW_{13}\ CO_2 + FARGONhum * GMW\_ARGON + FHO_2 * GMW\_H_2O \qquad \text{Eq. 4}$$

$$DF = Temp/(pBar * \Sigma GMW) \qquad \text{Eq. 5}$$

Thus, $DF_1$ constitutes the density factor computed at the original calibration time at the factory. As indicated by block 40 in FIG. 2A, this value is stored in the EEPROM memory 16 for later retrieval. A precision volume is injected through the pneumotach mouthpiece 30 (block 42). Flow is integrated over the duration of the injection, and $K_1$ is calculated using the equation:

$$K_1 = \text{KNOWN VOLUME}/\int\text{uncalibrated flow} \qquad \text{Eq. 6}$$

This quantity, $K_1$, is also stored in the nonvolatile memory 16 for later use (block 44).

With reference now to FIG. 2B, the steps employed in performing the dynamic calibration will be explained. First, the keyboard or on-board sensors are used to enter the relative humidity, barometric pressure and temperature at the test location at the time that a patient is to be evaluated (block 46). The same methodology as previously described using Eqs. 2–6 is used to calculate a new density factor, $DF_2$ (blocks 48–52). The previously stored density factor, $DF_1$, and the previously computed value $K_1$, are read out from the memory (block 54) and a new flow calibration factor is computed (block 56) using the formula:

$$K_2 = K_1(DF_2/DF_1)^{1.5} \qquad \text{Eq. 7}$$

Now, when it is desired to measure the flow of respiratory gases being breathed by the patient through the pneumotach mouthpiece, the new flow calibration factor, $K_2$, can be multiplied by the uncalibrated flow to obtain a calibrated flow reading (block 58) that is adjusted for variations in ambient conditions at the time of the patient test from those existing at the time of factory calibration.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of dynamically calibrating a flowmeter in a gas measuring system whose output varies with changes in ambient conditions of the gas being measured, comprising:

(a) entering at a first predetermined calibration time known as constants, a known temperature, a known barometric pressure and a known relative humidity:

(b) calculating a first density factor, $DF_1$, of said gas at said known temperature, said known barometric pressure and said known relative humidity;

(c) digitizing and storing said density factor, $DF_1$ in a nonvolatile memory of a microprocessor for later retrieval;

(d) injecting a known volume of a respiratory gas mixture having the calculated density factor, $DF_1$ through said flowmeter and determining the integral of uncalibrated flow;

(e) calculating a proportionality factor, $K_1$, by dividing said known volume by the integral of uncalibrated flow of the respiratory gas mixture;

(f) digitizing and storing said proportionality factor, $K_1$, in said nonvolatile memory of said microprocessor for later retrieval;

(g) sensing at a second later calibration time an ambient temperature, an ambient barometric pressure and an ambient relative humidity;

(h) calculating a second density factor, $DF_2$, of said gas using said ambient relative humidity;

(i) using said first density factor, $DF_1$, and said proportionality factor, $K_1$, stored in said nonvolatile memory and said calculated second density factor, $DF_2$, to compute a new proportionality constant, $K_1$; and (j) using said proportionality factor, $K_1$, to compute a calibrated flow reading adjusted for variations in ambient temperature, barometric pressure and relative humidity when the gas is being measured.

2. The method as in claim 1 wherein said density factors, $DF_1$ and $DF_2$, are computed as the quotient of the temperature in degrees Kelvin and the barometric pressure times the sum of the products of the fraction of each separate gas in an air mixture at room air ambient relative humidity times the gram molecular weight for that gas and the fraction of $H_2O$ times the gram molecular weight of $H_2O$ at the first calibration time and the second calibration time, respectively.

3. In a cardiopulmonary performance analyzer of the type having a microprocessor-based waveform analyzer including a memory for storing a program of instructions and operands, a flowmeter coupled to said waveform analyzer for providing an input thereto proportional to the volume rate of flow of inspired and expired air, a method for determining a proportionality factor for calibrating said flowmeter to take into account changes in temperature, barometric pressure and relative humidity from those prevailing at the time of factory calibration comprising the steps of:

A. at the time of factory calibration
(i) entering into said memory values of ambient relative humidity, atmospheric pressure and temperature;

(ii) storing in said memory various constants relating to the individual gas constituents of dry air;

(iii) calculating, using said stored values of relative humidity and barometric pressure and said constants relating to the individual gas constituents of dry air, the gas fractions at room air relative humidity, (iv) computing a density factor, $DF_1$, for the air present at the site and storing same in said memory;

(v) injecting a known precision volume of room air through said flowmeter while integrating a signal output of said flowmeter;

(vi) computing a calibration factor, $K_1$, by dividing said known precision volume by the integrated signal output of said flowmeter and storing said calibration factor, $K_1$, in said memory;

B. at the time of a test of cardiopulmonary performance on a patient at a field site;
(i) computing $DF_2$ by repeating the above steps (i), (iii) and (iv);

(ii) calculating a new calibration factor, $K_2$, using the stored calibration factor, $K_1$, the stored density factor, $D_1$, and the density factor determined at the field site, $DF_2$; and (iii) using said new calibration factor, $K_2$, to compute a calibrated flow reading adjusted for variations in ambient conditions at the time of the test of cardiopulmonary performance on a patient at a field site.

4. The method as in claim 3 wherein the various constants relating to the individual gas constituents of dry air include the fraction of each gas constituent of dry air and the gram molecular weight of each such gas constituent.

5. The method as in claim 3 wherein step (A)(iv) comprises:

dividing the air temperature in degrees Kelvin by the product of barometric pressure and the sum of the products of the gram molecular weight of each gas constituents of air and the fraction of each of said gas constituents in air at the ambient relative humidity.

* * * * *